United States Patent
Calderoni et al.

(10) Patent No.: US 12,193,884 B2
(45) Date of Patent: Jan. 14, 2025

(54) CONTACTLESS FORCE MEASUREMENT OF MOTOR TORQUE IN POWERED SURGICAL DEVICE

(71) Applicant: Covidien LP, Mansfield, MA (US)

(72) Inventors: Anthony D. Calderoni, Bristol, CT (US); David A. Nicholas, Trumbull, CT (US); John M. Pantazis, Stratford, CT (US); David A. Zeichner, Oxford, CT (US)

(73) Assignee: Covidien LP, Mansfield, MA (US)

( * ) Notice: Subject to any disclaimer, the term of this patent is extended or adjusted under 35 U.S.C. 154(b) by 564 days.

(21) Appl. No.: 17/517,884

(22) Filed: Nov. 3, 2021

(65) Prior Publication Data

US 2022/0151723 A1    May 19, 2022

Related U.S. Application Data (60) Provisional application No. 63/114,594, filed on Nov. 17, 2020.

(51) Int. Cl.
*A61B 90/00* (2016.01)
*A61B 17/115* (2006.01)
(Continued)

(52) U.S. Cl.
CPC ............ *A61B 90/06* (2016.02); *A61B 17/115* (2013.01); *G01L 3/1407* (2013.01);
(Continued)

(58) Field of Classification Search
CPC .............. A61B 90/06; A61B 2090/064; A61B 2090/066; G01L 3/1407–1457
See application file for complete search history.

(56) References Cited

U.S. PATENT DOCUMENTS

| 37,165 A | 12/1862 | Gary |
|---|---|---|
| 3,209,754 A | 10/1965 | Brown |

(Continued)

FOREIGN PATENT DOCUMENTS

| CN | 101683284 A | 3/2010 |
|---|---|---|
| CN | 102648864 A | 8/2012 |

(Continued)

OTHER PUBLICATIONS

Machine Translation of DE 102009057809 (Year: 2009).*

(Continued)

*Primary Examiner* — Nathaniel J Kolb (57) ABSTRACT

A surgical device includes a power source and a motor coupled to the power source. The device also includes a drive shaft having a proximal drive shaft having a proximal end portion coupled to the motor and a distal end portion, a proximal index gear coupled to the distal end portion of the proximal drive shaft, a distal drive shaft having a proximal end portion and a distal end portion, a distal index gear coupled to the proximal end portion of the distal drive shaft, a spring member biasedly coupling the proximal index gear and the distal index gear. The device also includes a force measurement sensor configured to measure rotation of the proximal index gear and the distal index gear. The device further includes a controller coupled to the force measurement sensor and configured to determine a force applied to the drive shaft based on a difference between rotation of the proximal index gear and the distal index gear.

11 Claims, 8 Drawing Sheets

(51) Int. Cl.
*G01L 3/14* (2006.01)
*A61B 17/00* (2006.01)
*A61B 17/11* (2006.01)

(52) U.S. Cl.
CPC .............. *A61B 2017/00022* (2013.01); *A61B 2017/00398* (2013.01); *A61B 2017/1132* (2013.01); *A61B 2090/066* (2016.02)

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,135,390 A * | 1/1979 | Templin ................ G01L 3/101 73/862.326 |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,027,663 A * | 7/1991 | Frister .................... G01L 3/1435 73/862.331 |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |

(56) References Cited

U.S. PATENT DOCUMENTS

| | | |
|---|---|---|
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |

(56) References Cited

U.S. PATENT DOCUMENTS

| | | |
|---|---|---|
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Ai-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |

(56) References Cited

U.S. PATENT DOCUMENTS

| | | |
|---|---|---|
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A2 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2018/0116737 A1* | 5/2018 | Bajo .................... G01L 3/1442 |
| 2018/0280096 A1* | 10/2018 | Allen .................... G01L 3/108 |

FOREIGN PATENT DOCUMENTS

| | | | |
|---|---|---|---|
| DE | 102009057809 A1 * | 6/2011 | .......... G01L 3/1457 |
| EP | 0537570 A2 | 4/1993 | |
| EP | 0647431 A2 | 4/1995 | |
| EP | 0738501 A1 | 10/1996 | |
| EP | 0770354 A1 | 5/1997 | |
| EP | 1070487 A2 | 1/2001 | |
| EP | 1201196 A1 | 5/2002 | |
| EP | 1658817 A1 | 5/2006 | |
| EP | 1813203 A2 | 8/2007 | |
| FR | 2 849 589 A1 | 7/2004 | |
| WO | 9414129 A1 | 6/1994 | |
| WO | 9729694 A1 | 8/1997 | |
| WO | 9740760 A1 | 11/1997 | |
| WO | 9837825 A1 | 9/1998 | |
| WO | 1999/52489 A1 | 10/1999 | |
| WO | 0234140 A2 | 5/2002 | |
| WO | 03026511 A1 | 4/2003 | |
| WO | 03030743 A2 | 4/2003 | |
| WO | 2004032760 A2 | 4/2004 | |
| WO | 2007030753 A2 | 3/2007 | |
| WO | 2007/114868 A2 | 10/2007 | |
| WO | 2007118179 A2 | 10/2007 | |
| WO | 2007014355 A3 | 4/2009 | |
| WO | 2009143092 A1 | 11/2009 | |

OTHER PUBLICATIONS

Detemple, P., "Microtechnology in Modern Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-ON-LINE, Electronic Component Manufacturers, pp. 1-2; Aug. 2013.

* cited by examiner

CONTACTLESS FORCE MEASUREMENT OF MOTOR TORQUE IN POWERED SURGICAL DEVICE

CROSS-REFERENCE TO RELATED APPLICATIONS

The present application claims the benefit and priority to U.S. Provisional Application No. 63/114,594 filed Nov. 17, 2020. The entire contents of which are incorporated herein by reference.

BACKGROUND

1. Technical Field

The present disclosure relates to surgical devices. More specifically, the present disclosure relates to handheld electromechanical surgical systems for performing surgical procedures.

2. Background of Related Art

Various medical devices, including handheld surgical devices and robotic devices, utilizes electrically powered motors and actuators to move joints and end effectors. In order to accurately control the motors, precise feedback from sensors is used to control various operating parameters of the motors. Parameters that are monitored include revolutions, torque, temperature, current draw, and the like. Thus, there is a continual need to provide more accurate sensors for measuring operating parameters of the motors to provide for precise control of the powered surgical devices.

SUMMARY

The present disclosure provides a system and method for measuring force and/or torque imparted on a drive shaft rotated by motors of a powered surgical device. The system includes a split output drive shaft having a proximal shaft and a distal shaft connected to one another by a mechanical spring member. The proximal shaft is coupled to the motor and the distal shaft is coupled to an end effector that receives external forces during use, e.g., due to tissue compression. When an external force is applied to the distal shaft while the motor is driving the proximal shaft, the connecting spring allows for rotational displacement of alignment to occur between the distal and proximal shafts, while maintaining a mechanical linkage between the proximal and distal shafts. The angle of displacement between the proximal and distal shafts is directly related to the amount of external force experienced by the distal shaft and the spring constant of the spring connecting the two shafts together. This angle of displacement is measured to determine the force being applied to the distal shaft. The angle may be measured in a variety of ways, including, but not limited to contactless manner using magnetic sensors. In embodiments, each of the proximal and distal shafts may have a toothed gear fixed to, with the "teeth" of the gear providing a segments readable by encoders (i.e. giant magnetoresistance sensors) to track the displacement between the proximal and distal shafts, whose outputs are being monitored by a controller (i.e., microprocessor).

According to one embodiment of the present disclosure a surgical device is disclosed. The surgical device includes a power source and a motor coupled to the power source. The device also includes a drive shaft having a proximal drive shaft having a proximal end portion coupled to the motor and a distal end portion, a proximal index gear coupled to the distal end portion of the proximal drive shaft, a distal drive shaft having a proximal end portion and a distal end portion, a distal index gear coupled to the proximal end portion of the distal drive shaft, a spring member biasedly coupling the proximal index gear and the distal index gear. The device also includes a force measurement sensor configured to measure rotation of the proximal index gear and the distal index gear. The device further includes a controller coupled to the force measurement sensor and configured to determine a force applied to the drive shaft based on a difference between rotation of the proximal index gear and the distal index gear.

Implementations of the above embodiment may include one or more of the following features. The proximal index gear includes a first plurality of teeth and the distal index gear includes a second plurality of teeth. The force measurement sensor may include a proximal force sensor disposed in proximity to the proximal index gear and configured to output a first signal based on a distance of the first plurality of teeth. The force measurement sensor may include a distal force sensor disposed in proximity to the distal index gear and configured to output a second signal based on a distance of the second plurality of teeth. The controller may be further configured to compare the first signal and the second signal to determine the force. The spring member has a circular shape having a center and includes a plurality of spokes extending from the center, each of the spokes having a grommet. A proximal index gear includes a first plurality of posts and a distal index gear includes a second plurality of posts. The first plurality of posts and the second plurality of posts are configured to be inserted into the grommets. The surgical device may further include a position measurement sensor having a proximal position sensor and a distal position sensor. The proximal index gear includes a proximal index mark and the proximal position sensor is configured to detect passage of the proximal index mark as the proximal index gear is rotated. The distal index gear includes a distal index mark and the distal position sensor is configured to detect passage of the distal index mark as the distal index gear is rotated.

According to another embodiment of the present disclosure a surgical device is disclosed. The surgical device includes a power source and a motor coupled to the power source. The device also includes a drive shaft having a proximal drive shaft having a proximal end portion coupled to the motor, a distal drive shaft, a spring member biasedly coupling the proximal drive shaft and the distal drive shaft. The device also includes a force measurement sensor configured to measure a difference in rotation between the proximal drive shaft and the distal drive shaft. The device further includes a controller coupled to the force measurement sensor and configured to determine a force applied to the drive shaft based on the difference in rotation between the proximal drive shaft and the distal drive shaft.

Implementations of the above embodiment may include one or more of the following features. The drive shaft may include a proximal index gear coupled to a distal end portion of the proximal drive shaft, the proximal index gear including a first plurality of teeth; and a distal index gear coupled to a proximal end portion of the distal drive shaft, the distal index gear includes a second plurality of teeth. The force measurement sensor includes a proximal force sensor disposed in proximity to the proximal index gear and configured to output a first signal based on a distance of the first plurality of teeth. The force measurement sensor includes a distal force sensor disposed in proximity to the distal index gear and configured to output a second signal based on a distance of the second plurality of teeth. The controller may be further configured to compare the first signal and the second signal to determine the force. The spring member has a circular shape having a center and includes a plurality of spokes extending from the center, each of the spokes having a grommet. A proximal index gear includes a first plurality of posts and a distal index gear includes a second plurality of posts, the first plurality of posts and the second plurality of posts are configured to be inserted into the grommets. The surgical device may include: a position measurement sensor including a proximal position sensor and a distal position sensor. The proximal index gear includes a proximal index mark and the proximal position sensor is configured to detect passage of the proximal index mark as the proximal index gear is rotated. The distal index gear includes a distal index mark and the distal position sensor is configured to detect passage of the distal index mark as the distal index gear is rotated.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a force measurement sensor for monitoring operation of a motor. The motor may be used in any powered or robotic surgical device, such as a powered surgical device 1. The stapler 1 has a handle assembly, an adapter assembly coupled to the handle assembly, and an end effector coupled to the adapter assembly. The stapler allows for full, independent control of three functions: clamping, stapling, and cutting.

Figure 1:
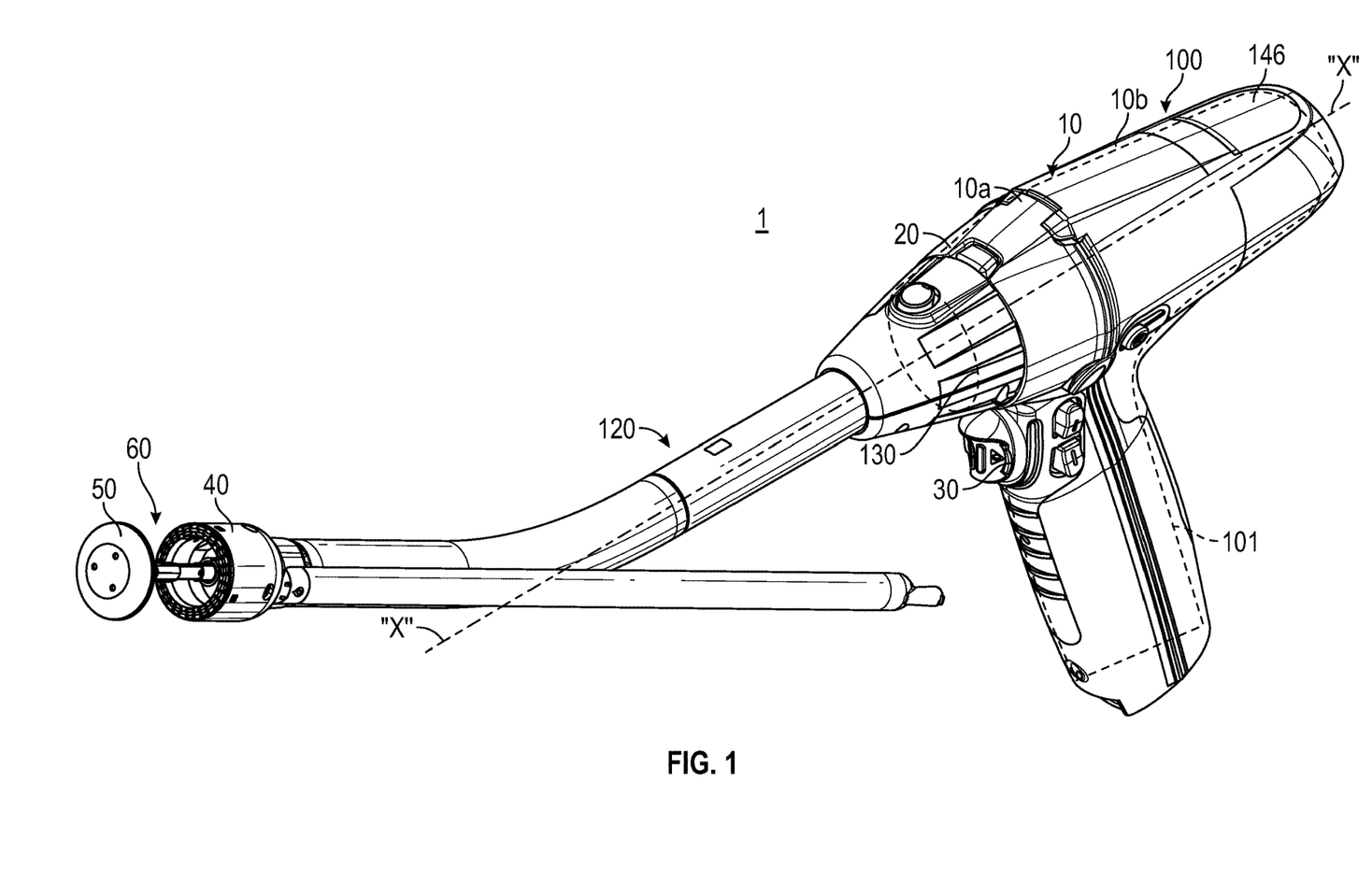
FIG. 1 is a perspective view of a handheld surgical instrument including a handle assembly, an adapter assembly, and an end effector, according to an embodiment of the present disclosure.

FIG. 1 illustrates a surgical device, such as, for example, a powered surgical device 1 for forming end-to-end anastomosis ("EEA"), including a handle assembly 100, which is configured for selective connection with an adapter assembly 120. The adapter assembly 120 is configured for selective connection with an end effector 60, which includes a reload 40 and an anvil assembly 50. The end effector 60 is configured to produce a surgical effect on tissue of a patient, namely, forming an anastomosis by connecting two portions of a structure (e.g., intestine, colon, etc.) by clamping, stapling, and cutting tissue grasped within the end effector 60.

The handle assembly 100 includes a power handle 101 and an outer shell housing 10 configured to selectively receive and encase power handle 101. The shell housing 10 includes a distal half-section 10a and a proximal half-section 10b pivotably connected to distal half-section 10a. When joined, distal and proximal half-sections 10a, 10b define a shell cavity therein in which power handle 101 is disposed.

Distal and proximal half-sections 10a, 10b of shell housing 10 are divided along a plane that traverses a longitudinal axis "X" of adapter assembly 120. Distal half-section 10a of shell housing 10 defines a connecting portion 20 configured to accept a corresponding drive coupling assembly 130 of adapter assembly 120. Distal half-section 10a of shell housing 10 supports a toggle control button 30. Toggle control button 30 is capable of being actuated in four directions (e.g., a left, right, up and down).

Figure 2:
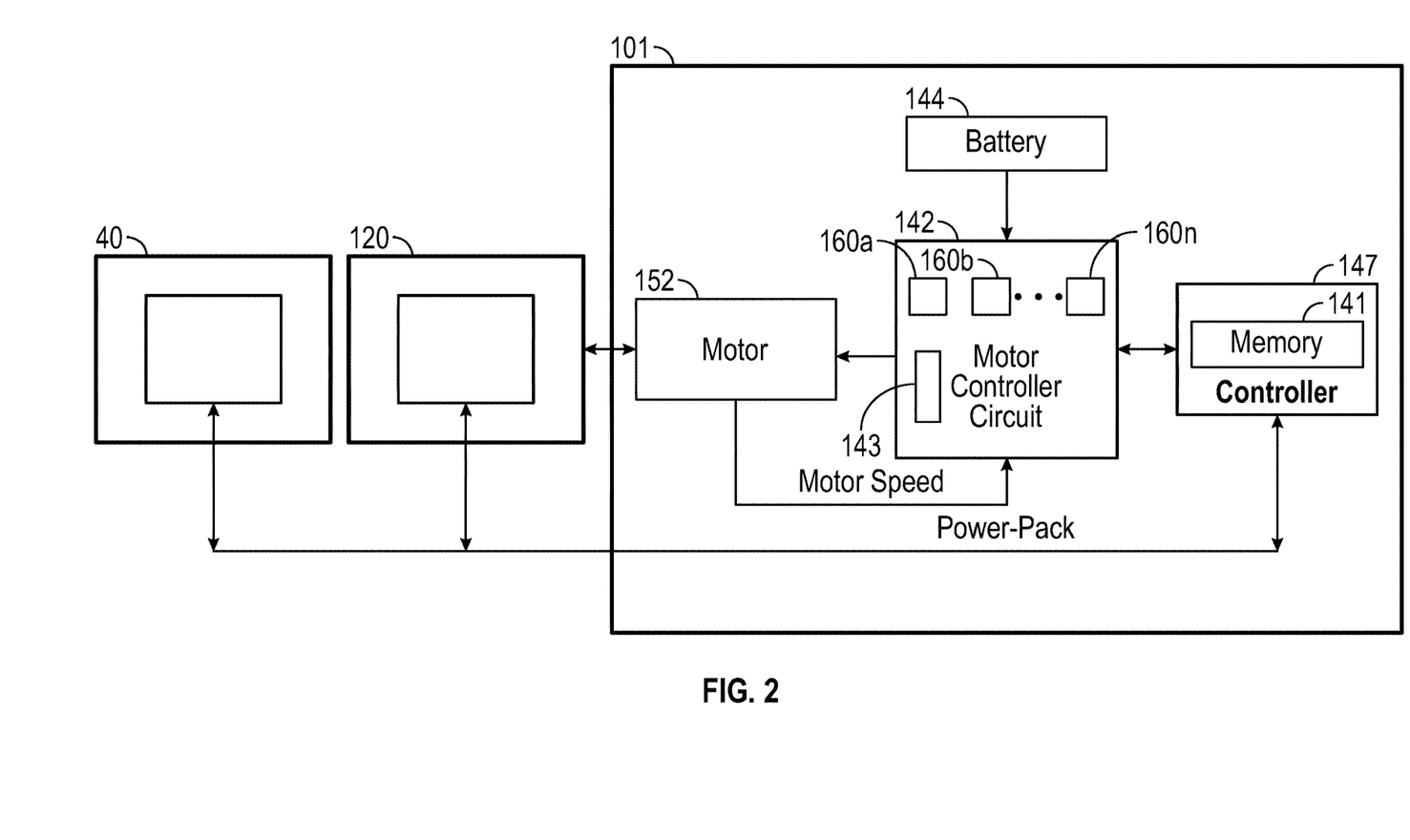
FIG. 2 is a schematic diagram of the handle assembly, the adapter assembly, and the end effector of FIG. 1.
Figure 3:
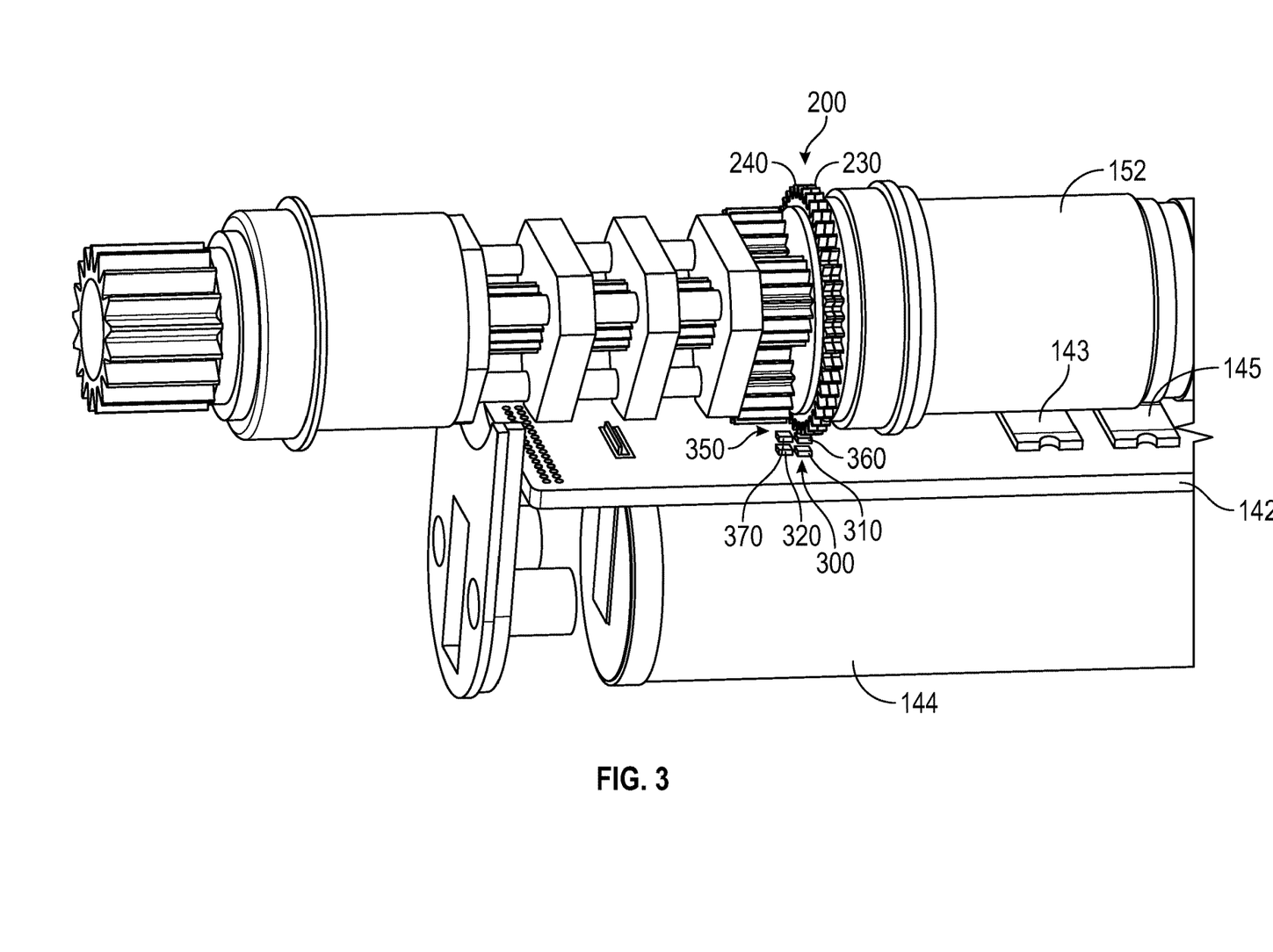
FIG. 3 is a perspective view of components of the handle assembly of FIG. 1.

With reference to FIGS. 1-3, the power handle 101 includes a printed circuit board (PCB) 142, a rechargeable battery 144 configured to supply power to any of the electrical components of handle assembly 100, and a plurality of motors 152 coupled to the battery 144. The power handle 101 also includes a display 146. In embodiments, the motors 152 may be coupled to any suitable power source configured to provide electrical energy to the motor 152, such as an AC/DC transformer. Each of the motors 152 is coupled a motor controller 143 which controls the operation of the corresponding motor 152 including the flow of electrical energy from the battery 144 to the motor 152. A main controller 147 may be disposed on the PCB 142 and controls the power handle 101. The main controller 147 is configured to execute software instructions embodying algorithms disclosed herein, such as clamping, stapling, and cutting algorithms which control operation of the power handle 101.

The motor controller 143 may be disposed on the PCB 142 includes a plurality of sensors 160a . . . 160n configured to measure operational states of the motor 152 and the battery 144. The sensors 160a-n may include strain gauges, voltage sensors, current sensors, temperature sensors, telemetry sensors, optical sensors, and combinations thereof. The sensors 160a-160n may measure voltage, current, and other electrical properties of the electrical energy supplied by the battery 144. The sensors 160a-160n may also measure angular velocity (e.g., rotational speed) as revolutions per minute (RPM), torque, temperature, current draw, and other operational properties of the motor 152. The sensor 160a also includes an encoder configured to count revolutions or other indicators of the motor 152, which is then use by the main controller 147 to calculate linear movement of components movable by the motor 152. Angular velocity may be determined by measuring the rotation of the motor 152 or a drive shaft (not shown) coupled thereto and rotatable by the motor 152. The position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 120 and/or the end effector 60 by counting revolutions of the motor 152.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions. The main controller 147 is also configured to accept a plurality of user inputs from a user interface (e.g., switches, buttons, touch screen, etc. coupled to the main controller 147). The main controller 147 is also coupled to a memory 141. The memory 141 may include volatile (e.g., RAM) and non-volatile storage configured to store data, including software instructions for operating the power handle 101.

The power handle 101 includes a plurality of motors 152 each including a respective drive shaft 200 (FIG. 4) extending therefrom and configured to drive a respective transmission assembly. Rotation of the motor shafts by the respective motors 152 function to drive shafts and/or gear components of adapter assembly 120 in order to perform the various operations of handle assembly 100. In particular, motors 152 of power handle 101 are configured to drive shafts and/or gear components of adapter assembly 120 in order to selectively extend/retract the anvil assembly 50 to open/close end effector 60, fire an annular array of staples of reload 40, and move an annular knife (not explicitly shown) of reload 40.

Figure 4:
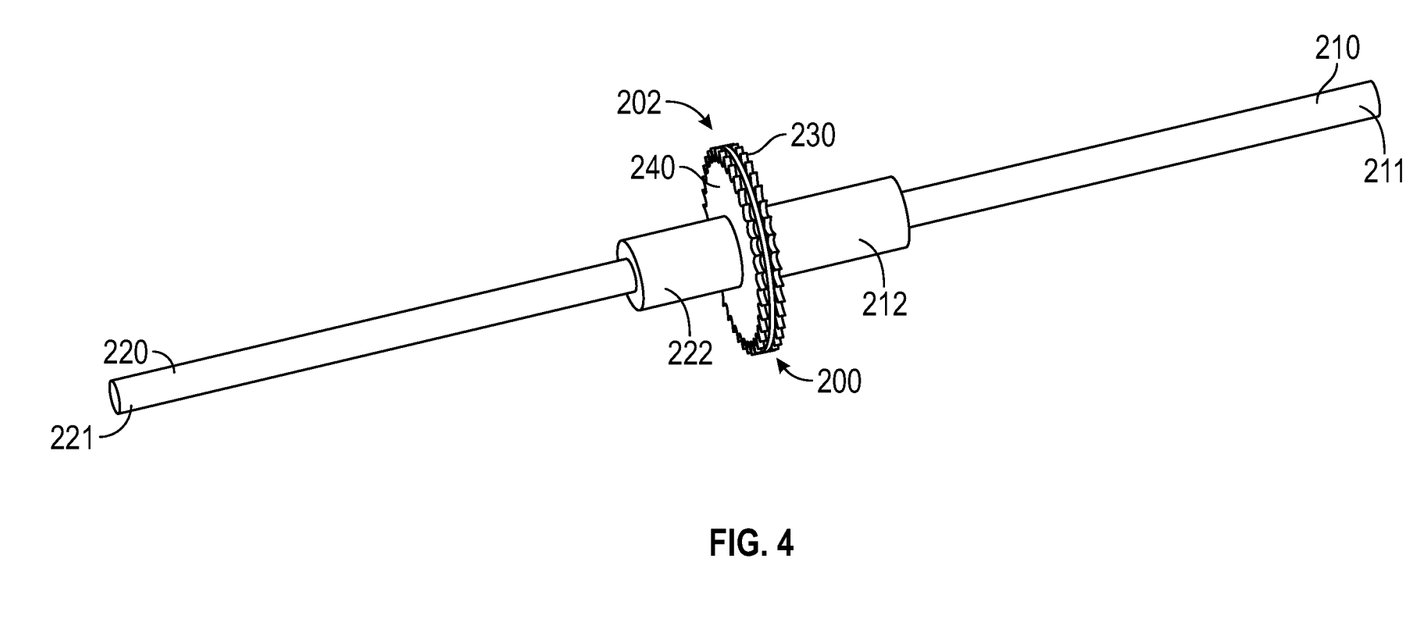
FIG. 4 is a perspective view of a drive shaft and a force transfer assembly according to the present disclosure.
Figure 5:
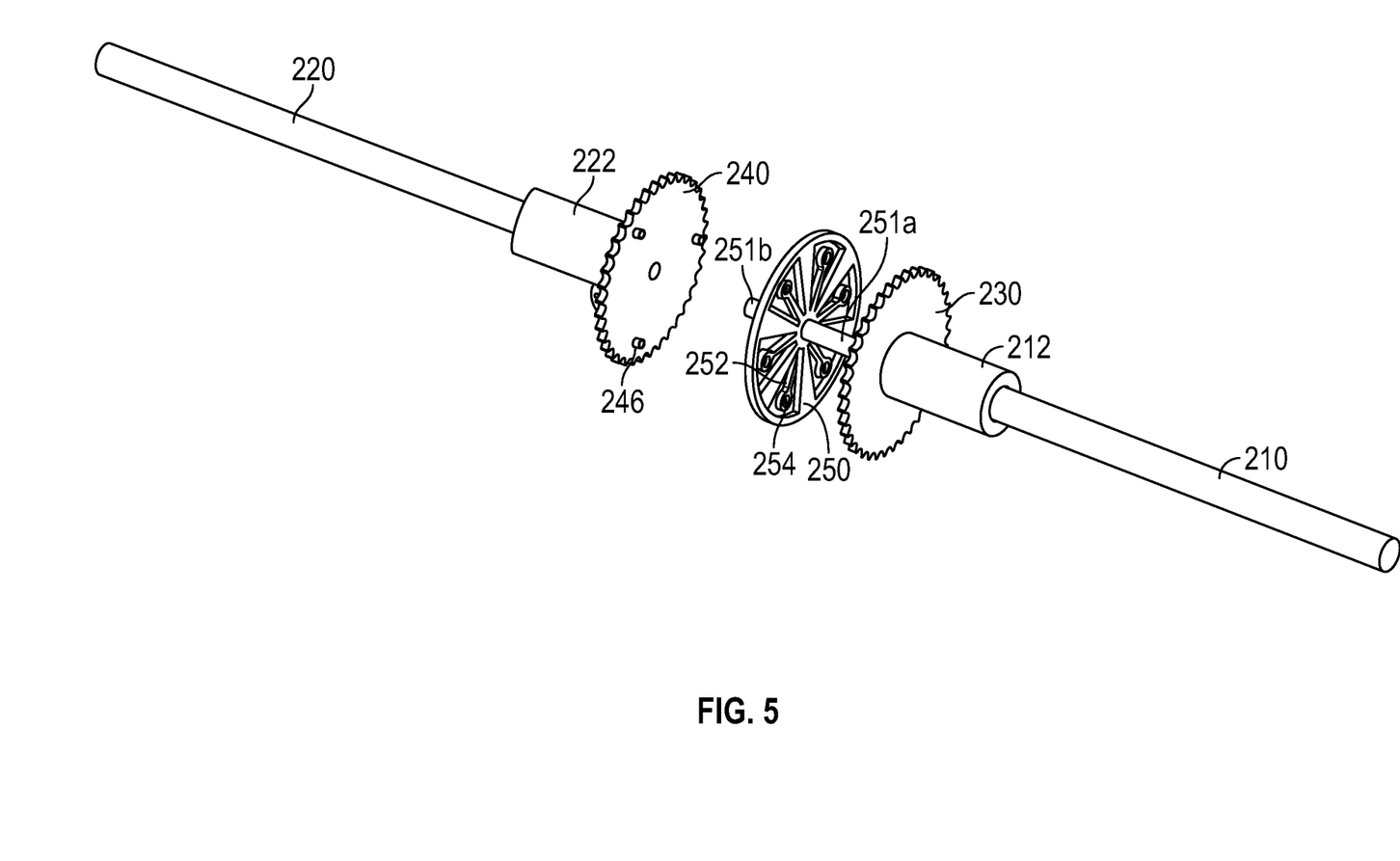
FIG. 5 is a perspective view of the drive shaft and the force measurement sensor with a proximal shaft and a distal shaft separated according to the present disclosure.

With reference to FIGS. 4 and 5, the drive shaft 200 includes a proximal shaft 210 and a distal shaft 220 and a force transfer assembly 202 interconnecting the proximal and distal shafts 210 and 220. The drive shaft 200 includes The drive shaft 200 may be disposed within the power handle 101 and the proximal shaft 210 is coupled to and/or disposed within the motor 152 and is rotatable by the motor 152. The distal shaft 220 is coupled to a component of the powered surgical device 1 that is being actuated, e.g., end effector 60. The proximal shaft 210 includes a proximal end portion 211 and a distal end portion 212. The distal end portion 212 of the proximal shaft 210 includes a proximal index gear 230. The distal shaft 220 includes a proximal end portion 221 and a distal end portion 222. The proximal end portion 221 of the distal shaft 220 includes a distal index gear 240.

Figure 6:
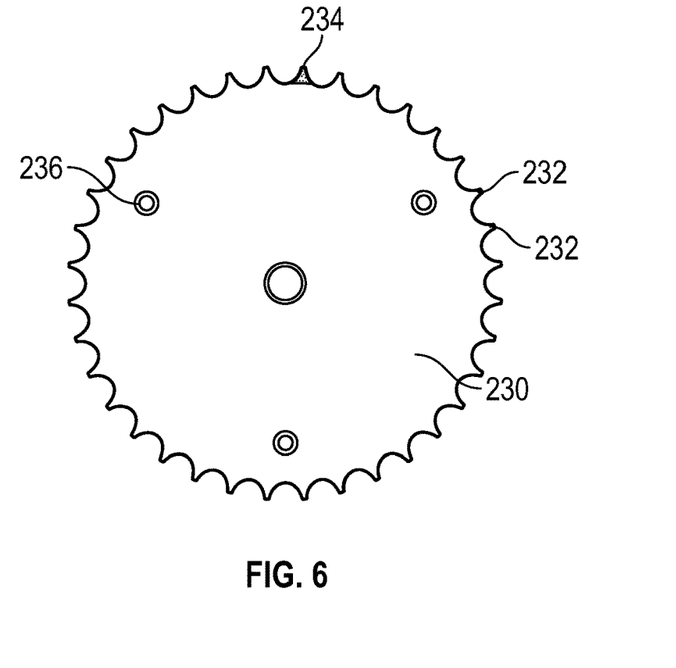
FIG. 6 is a front view of an index gear coupled to each of the proximal shaft and the distal shaft of the drive shaft of FIG. 3.

The index gears 230 and 240 are identical and are described with respect to the proximal index gear 230 as shown in FIG. 6. The index gear 230 includes a plurality of teeth 232 disposed along a perimeter of the index gear 230. One or more of the teeth 232 may be an index mark 234, that is used to count number of rotations of the proximal shaft 210. Similarly, the distal index gear 240 includes an index mark 244 (FIG. 7) to count the number of rotations of the distal shaft 220. The proximal index gear 230 and the distal index gear 240 also include a plurality of posts 236 and 246, which are used to mechanically couple to a spring member 250. The force transfer assembly 202 includes the index gears 230 and 240 and the spring member 250 disposed therebetween.

With reference to FIG. 5, the spring member 250 has a substantially circular shape and includes a plurality of spokes 252, each of which radiates from the center of the spring member 250 to a grommet 254, which is configured to receive the posts 236. The number of grommets 254 corresponds to the combined number of posts 236 of the proximal index gear 230 and the number of posts 246 of the distal index gear 240. As shown in FIGS. 5 and 6, each of the plurality of posts 236 and 246 may be arranged in a polygonal pattern, such that the plurality of posts 236 and 246 are aligned with the grommets 254.

The spring member 250 may be formed from metal or any other suitable elastic material. The spring member 250 interconnects the proximal shaft 210 and the distal shaft 220 since the posts 236 and 246 are inserted in the grommets 254. In embodiments, the spring member 250 may have a proximal post 251a and a distal post 251b configured to be inserted into the proximal shaft 210 and the distal shaft 220, respectively. This configuration further secures and aligns the spring member 250 with the proximal and distal shafts 210 and 220. Each of the spokes 252 acts as a spring since one end of the spokes 252 is attached to the center of the spring member 250 and another end terminated with the grommet 254 freely movable, i.e., bendable, by the posts 236 and 246. The degree to which the spokes 252 are bendable is based on the spring constant of the spokes 252, which depends on the dimensions and the material of the spokes 252. The spring constant may be selected to provide for 1:1 rotation of the proximal and distal shafts 210 and 220 during normal operation while allowing for deflection at a preset rate in response to external forces being applied to the distal shaft 220.

Figure 7:
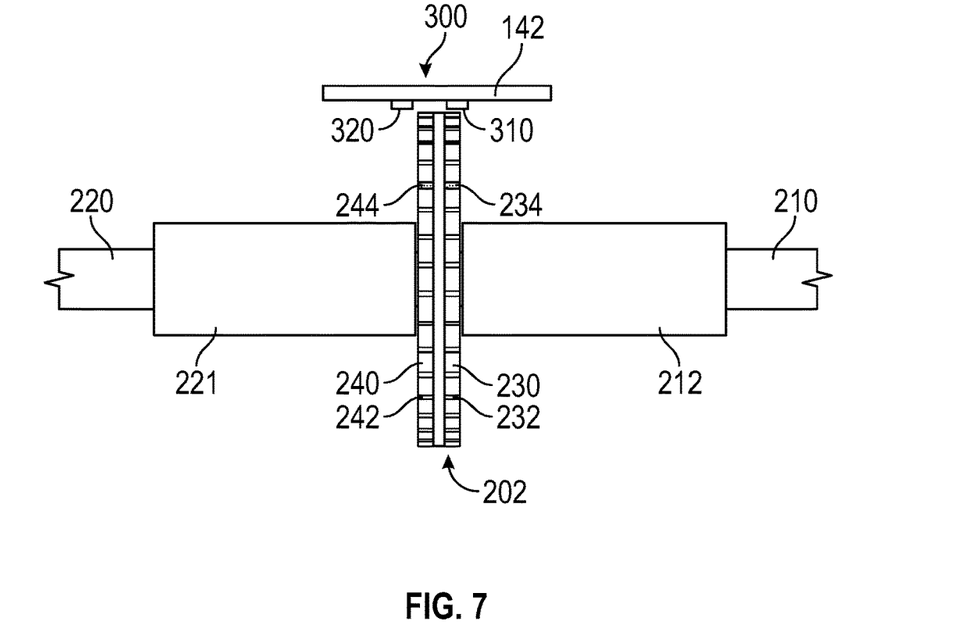
FIG. 7 is a top view of the proximal shaft and the distal shaft of the drive shaft of FIG. 3 with the index gears aligned.
Figure 8:
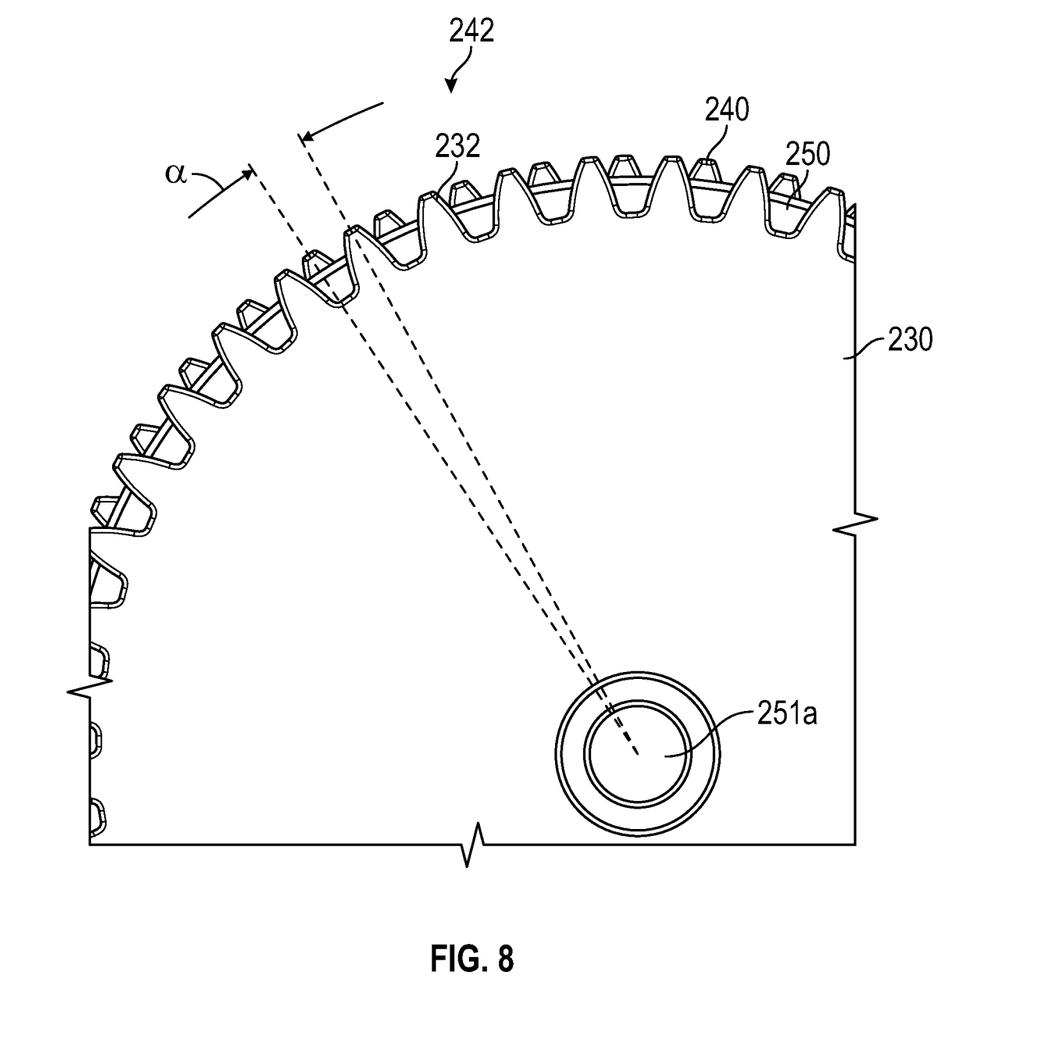
FIG. 8 is a front view of the index gears in a misaligned configuration.

The spring member 250 biasedly couples the proximal shaft 210 and the distal shaft 220. Thus, as the proximal shaft 210 is rotated, the spring member 250 transfers rotation to the distal shaft 220. However, once the distal shaft 220 encounters resistance, the spokes 252 are biased in direction opposite the direction in which the proximal shaft 210 is being rotated. During normal operation, when there is no external force acting on the distal shaft 220, the proximal and distal index gears 230 and 240 are aligned as shown in FIG. 7. Upon encountering sufficient external force, i.e., force that bends the spokes 252, the proximal and distal index gears 230 and 240 come out of alignment as shown in FIG. 8. The degree of misalignment is indicated by an angle between corresponding teeth 232 and 242. Measurement of the misalignment, i.e., the angle, between the teeth 232 and 242 allows for determination of the force encountered by the distal shaft 220.

With reference to FIG. 7, a force measurement sensor 300 includes a proximal sensor 310 and a distal sensor 320. The proximal and distal sensors 310 and 320 are disposed in proximity with proximal and distal index gear 230 and 240, respectively. The proximal and distal sensors 310 and 320 are configured to output a signal based on the distance of the teeth 232 and 242 of the proximal and distal index gears 230 and 240, which are formed or otherwise include a ferromagnetic material. The proximal and distal sensors 310 and 320 may be magnetic sensors, such as Reed, Hall, and Giant Magneto-Resistive (GMR) sensors. Thus, the proximal and distal index gears 230 and 240 are aligned, the teeth 232 and 242 are also in alignment, as shown in FIG. 7. As such, the proximal and distal sensors 310 and 320 output the same signal as the proximal and distal index gears 230 and 240 are rotated in unison. The signals may be sinusoidal wave with the peaks corresponding to teeth 232 and 242 approximating the proximal and distal sensors 310 and 320. Upon encountering sufficient external force, i.e., force that bends the spokes 252, the proximal and distal index gears 230 and 240 come out of alignment as shown in FIG. 8. Since the teeth 232 and 242 are not aligned, the readings of the proximal and distal sensors 310 and 320 also differ, i.e., peaks of the signals are misaligned as well. The signals from the proximal and distal sensors 310 and 320 are transmitted to the main controller 147, which correlates the degree of misalignment, i.e., angle α, between the teeth 232 and 242 with the force encountered by the distal shaft 220. Thus, the main controller 147 determines a force applied to the drive shaft 200 based on an angular difference in rotation between the proximal drive shaft 210 and the distal drive shaft 220. The main controller 147 is further configured to control the motor 152 based on the measured force. Controlling the motor 152 may include adjusting rotation speed in response to measured force, i.e., lowering the speed in response to detection of increased force.

With reference to FIG. 3, a position measurement sensor 350 includes a proximal sensor 360 and a distal sensor 370. The proximal and distal sensors 360 and 370 are configured to track rotation of the proximal and distal index gears 230 and 240 and count the number and/or degree of rotations of the proximal and distal shafts 210 and 220. The proximal and distal sensors 360 and 370 may be magnetic sensors, such as the proximal and distal sensors 310 and 320. The proximal and distal sensors 360 and 370 may be optical sensors, i.e., encoders, configured to track the index marks 234 and 244 disposed on each of the proximal and distal index gears 230 and 240, respectively. The index marks 234 and 244 may be a tooth that is different from the other teeth 232 and 242, i.e., different size and/or shape, or the index marks 234 and 244 may be a missing tooth. In embodiments where proximal and distal sensors 360 and 370 are optical sensors, the index marks 234 and 244 may be of different color than the other teeth 232 and 242. The proximal and distal sensors 360 and 370 output a signal every time the index marks 234 and 244 are detected. The signal is transmitted to the main controller 147, which maintains a count of the signals, thereby counting the number of revolutions of each of the proximal and distal shafts 210 and 220. The main controller 147 may utilize the count totals to determine the longitudinal distance traveled by the components actuated by the drive shaft 200.

Figure 9:
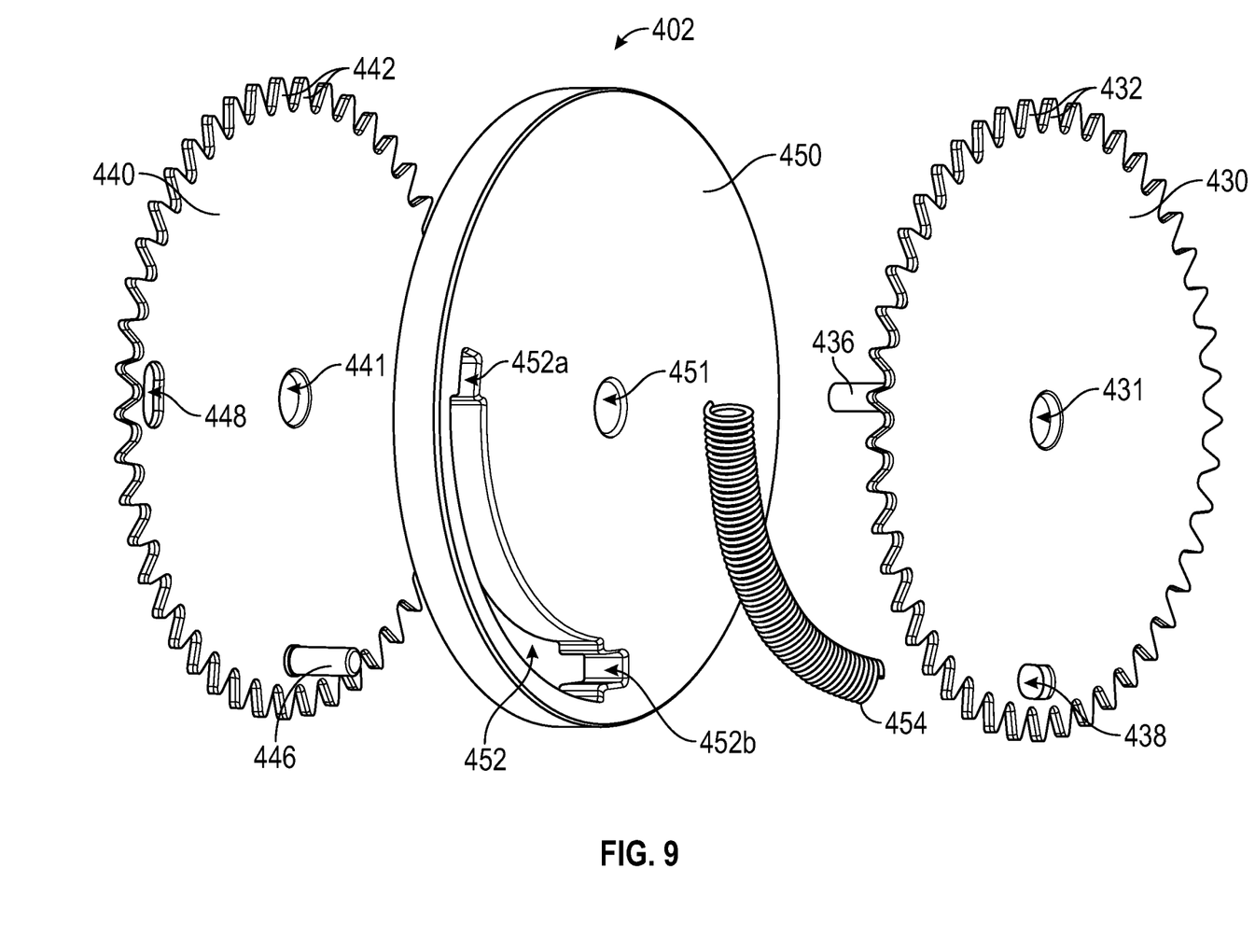
FIG. 9 is a perspective view of a force transfer assembly according to another embodiment of the present disclosure.

With reference to FIG. 9, another embodiment of a force transfer assembly 402 is shown. The force transfer assembly 402 includes a proximal index gear 430, a distal index gear 440, and a spring assembly 450 disposed therebetween. The distal end portion 212 of the proximal shaft 210 is coupled to the proximal index gear 430 and the proximal end portion 221 of the distal shaft 220 is coupled to the distal index gear 440. Each of the proximal index gear 430, the distal index gear 440, and the spring assembly 450 may define a respective central opening 431, 441, 451 therethrough to allow for coupling of the proximal shaft 210 and the distal shaft 220 to each other through the proximal index gear 430, the distal index gear 440, and the spring assembly 450.

The spring assembly 450 has a substantially circular shape having an arcuate slit 452 defined through the spring assembly 450. The arcuate slit 452 has a first end 452a and a second end 452b and may have an angle from about 10° to about 180°. The arcuate slit 452 is configured to house a spring member 454, which conforms to the arcuate shape of the slit 452. The spring member 454 may be a spiral spring. The proximal index gear 430 includes a plurality of teeth 432 disposed along a perimeter of the index gear 430. The proximal index gear 430 also includes a post 436 facing the spring assembly 450 and an opening 438.

The distal index gear 440 includes a plurality of teeth 442 disposed along a perimeter of the index gear 440. The distal index gear 440 also includes a post 446 facing the spring assembly 450 and an opening 448. When the proximal index gear 430, the distal index gear 440, and the spring assembly 450 are in contact with each other. The post 436 is disposed at the first end 452a of the arcuate slit 452 and extends into the opening 448 of distal index gear 440. Similarly, the post 446 is disposed at the second end 452b of the arcuate slit 452 and extends into the opening 438 of the proximal index gear 430. Since the spring member 454 is disposed within the arcuate slit 452 and between the posts 436 and 446 of the proximal and distal index gears 430 and 440, respectively, the spring member 454 pushes the posts 436 and 446 in opposite directions.

The spring member 454 biasedly couples the proximal shaft 210 and the distal shaft 220. Thus, as the proximal shaft 210 is rotated, the spring member 454 transfers rotation to the distal shaft 220. However, once the distal shaft 220 encounters resistance, the spring member 454 is compressed between the posts 436 and 446. During normal operation, when there is no external force acting on the distal shaft 220, the proximal and distal index gears 430 and 440 are aligned (as shown in FIG. 7 with respect to the index gears 230 and 240). Upon encountering sufficient external force, i.e., force that compresses the spring member 454, the proximal and distal index gears 430 and 440 come out of alignment (as shown in FIG. 8 with respect to the index gears 230 and 240). The degree of misalignment is indicated by an angle between corresponding teeth 432 and 442. Measurement of the misalignment, i.e., the angle, between the teeth 432 and 442 allows for determination of the force encountered by the distal shaft 220. The same force measurement sensor 300 of FIGS. 3 and 7 may be used to detect misalignment and measure the force.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a power source;
   a motor coupled to the power source;
   a drive shaft including:
      a proximal drive shaft having a proximal end portion coupled to the motor and a distal end portion;
      a proximal index gear coupled to the distal end portion of the proximal drive shaft;
      a distal drive shaft having a proximal end portion and a distal end portion;
      a distal index gear coupled to the proximal end portion of the distal drive shaft;
      a spring member biasedly coupling the proximal index gear and the distal index gear;
   a measurement unit comprising:
      a first distance sensor configured to output a first signal indicative of a first distance between the first distance sensor and a toothed edge of the proximal index gear; and
      a second distance sensor configured to output a second signal indicative of a second distance between the second distance sensor and a toothed edge of the distal index gear; and
   a controller coupled to the measurement unit and configured to:
      determine a first rotation of the proximal index gear based on the first signal;
      determine a second rotation of the distal index gear based on the second signal; and
      determine a force applied to the drive shaft based on a difference between the first rotation and the second rotation.

2. The surgical device according to claim 1, wherein the spring member has a circular shape having a center and includes a plurality of spokes extending from the center, each spoke of the plurality of spokes having a grommet.

3. The surgical device according to claim 2, wherein the proximal index gear includes a first plurality of posts and the distal index gear includes a second plurality of posts, wherein the first plurality of posts and the second plurality of posts are configured to be inserted into the grommets.

4. The surgical device according to claim 1, further comprising:
   a proximal position sensor configured to output a first rotation signal indicative of a rotational distance traveled by the proximal index gear; and
   a distal position sensor configured to output a second rotation signal indicative of a rotational distance traveled by the distal index gear;
   wherein the distal drive shaft is configured to actuate a surgical end effector, and the controller is configured to determine a longitudinal distance traveled by the surgical end effector based on the first and second rotation signals.

5. The surgical device according to claim 4, wherein at least one of the proximal index gear or the distal index gear includes an index mark for detection by the corresponding at least one of the proximal position sensor or the distal position sensor during rotation.

6. The surgical device according to claim 5, wherein the index mark comprises a surface portion having at least one of a predetermined color, a predetermined shape, or a predetermined size, for detection by the at least one of the first distance sensor or the second distance sensor.

7. A surgical device, comprising:
   a power source;
   a motor coupled to the power source;
   a drive shaft coupled to the motor and comprising:
      a proximal drive shaft having a proximal index gear;
      a distal drive shaft configured to actuate a surgical end effector and having a distal index gear; and
      a spring member biasedly coupling the proximal drive shaft to the distal drive shaft;
   a first sensor configured to output a first signal indicative of a first distance to the proximal index gear; and
   a second sensor configured to output a second signal indicative of a second distance to the distal index gear; and
   a controller receiving the first signal and the second signal, and configured to determine an applied force to the drive shaft based on a difference between the first distance and the second distance.

8. The surgical device according to claim 7, wherein at least one of the first distance or the second distance is defined with respect to an outer edge portion of the corresponding at least one of the proximal index gear or the distal index gear.

9. The surgical device according to claim 8, wherein at least one of the proximal index gear or the distal index gear comprises radially-projecting gear teeth at least partially defining the outer edge portion.

10. The surgical device according to claim 7, further comprising:
    a proximal position sensor configured to output a first rotation signal indicative of a rotational distance traveled by the proximal index gear; and
    a distal position sensor configured to output a second rotation signal indicative of a rotational distance traveled by the distal index gear;
    wherein the controller is further configured to determine a longitudinal distance traveled by the surgical end effector based on the first and second rotation signals.

11. The surgical device according to claim 10, wherein at least one of the proximal index gear or the distal index gear comprises an outer edge portion having an index mark for detection by the corresponding at least one of the proximal position sensor or the distal position sensor.

* * * * *